United States Patent
Leeming et al.

(10) Patent No.: US 9,459,260 B2
(45) Date of Patent: Oct. 4, 2016

(54) DETECTION OF DIAGNOSTIC PEPTIDES

(75) Inventors: Diana Julia Leeming, Espergaerde (DK); Morten Karsdal, Kobenhavn O (DK); Efstathios Vassiliadis, Rodovre (DK)

(73) Assignee: Nordic Bioscience A/S, Herlev (DK)

( * ) Notice: Subject to any disclaimer, the term of this patent is extended or adjusted under 35 U.S.C. 154(b) by 99 days.

(21) Appl. No.: 14/122,349

(22) PCT Filed: May 23, 2012

(86) PCT No.: PCT/EP2012/059636
§ 371 (c)(1),
(2), (4) Date: Mar. 28, 2014

(87) PCT Pub. No.: WO2012/163768
PCT Pub. Date: Dec. 6, 2012

(65) Prior Publication Data
US 2015/0125964 A1    May 7, 2015

(30) Foreign Application Priority Data

May 27, 2011  (GB) .................................. 1108970.3
Jul. 5, 2011   (GB) .................................. 1111469.1

(51) Int. Cl.
*G01N 31/00*   (2006.01)
*G01N 33/53*   (2006.01)
*G01N 33/68*   (2006.01)
*G01N 33/564*  (2006.01)
*C07K 16/18*   (2006.01)

(52) U.S. Cl.
CPC ........... *G01N 33/6887* (2013.01); *C07K 16/18* (2013.01); *G01N 33/564* (2013.01); *G01N 33/6842* (2013.01); *G01N 2333/78* (2013.01); *G01N 2800/102* (2013.01)

(58) Field of Classification Search
CPC ............. C07K 16/26; G01N 2333/59; G01N 2800/368; Y10S 436/814
See application file for complete search history.

(56) References Cited

U.S. PATENT DOCUMENTS 9,206,464 B2 * 12/2015 Veidal ....................... C12Q 1/37
2008/0026485 A1    1/2008 Hueber

FOREIGN PATENT DOCUMENTS

| WO | 2009007846 A2 | 1/2009 | |
|---|---|---|---|
| WO | 2010115749 A2 | 10/2010 | |
| WO | 2010117694 A2 | 10/2010 | |
| WO | WO 2010/117694 A2 * | 10/2010 | ............ C07K 14/47 |

OTHER PUBLICATIONS

Pratesi et al. (Clinical and Experimental Immunology, vol. 164, 2011, pp. 337-345).*

Nicholas Ap et al. Preparation of a monoclonal antibody to citrullinated epitopes: its characterization and some applications to immunohistochemistry in human brain. Glia 2002; vol. 37: pp. 328-336.

Raats, JHM et al. Recombinant human monoclonal autoantibodies specific for citrulline-containing peptides from phage display libraries derived from patients with rheumatoid arthritis. J Rheumatology 2003; vol. 38: pp. 1696-1711.

Takizawa, Y et al. Citrullinated fibrinogen detected as a soluble citrullinated autoantigen in rheumatoid arthritis synovial fluids. Ann Rheum Dis. 2006; vol. 65: pp. 1013-1020.

Chang, X et al. Citrullination of fibronectin in rheumatoid arthritis synovial tissue. Rheumatology (Oxford). 2005; vol. 44: pp. 1374-1382.

Van Steendam, K et al. Citrullinated vimentin as an important antigen in immune complexes from synovial fluid of rheumatoid arthritis patients with antibodies against citrullinated proteins. Arthritis Res Ther. 2010; vol. 12: R132.

Tabushi, Y et al. Detection of citrullinated proteins in synovial fluids derived from patients with rheumatoid arthritis by proteomics-based analysis. Ann Clin Biochem. 2008; vol. 45: pp. 413-417.

Tilleman K et al. Synovial detection and autoantibody reactivity of processed citrullinated isoforms of vimentin in inflammatory arthritides. Rheumatology (Oxford). 2008; vol. 47: pp. 597-604.

Lundberg, K et al. Citrullinated proteins have increased immunogenicity and arthritogenicity and their presence in arthritic joints correlates with disease severity. Arthritis Res Ther. 2005; vol. 7(3): R458-R467.

Van Gaalen, et al. A comparison of the diagnostic accuracy and prognostic value of the first and second anti-cyclic citrullinated peptides (CCP1 and CCP2) autoantibody tests for rheumatoid arthritis. Ann Rheum Dis. 2005; vol. 64: pp. 1510-1512.

Lutgens, LCHW et al. Citrulline: a physiologic marker enabling quantitation and monitoring of epithelial radiation-induced small bowel damage. Int J Radiat Oncol Biol Phys. 2003; vol. 57: pp. 1067-1074.

Schellekens, GA et al. Citrulline is an essential constituent of antigenic determinants recognized by rheumatoid arthritis-specific autoantibodies. J Clin Invest 1998; vol. 101: pp. 273-281.

Uysal, H et al. Structure and pathogenicity of antibodies specific for citrullinated collagen type II in experimental arthritis. J Exp Med. 2009; vol. 206: pp. 449-462.

Zhao, X et al. Circulating immune complexes contain citrullinated fibrinogen in rheumatoid arthritis. Arthritis Res Ther. 2008; vol. 10: R94.

* cited by examiner

*Primary Examiner* — Lisa Cook
(74) *Attorney, Agent, or Firm* — Benjamin Aaron Adler

(57) ABSTRACT

An assay for citrullinated fragments of SOCS-2, Alpha 1 anti tyrpsin, versican, biglycan, laminin, or other protein having a terminal antibody binding site comprising citrulline in a blood derived sample shows diagnostic relevance in relation to rheumatoid arthritis or fibrotic disease.

9 Claims, 3 Drawing Sheets

SEQUENCE LISTING

```
<160> NUMBER OF SEQ ID NOS: 31

<210> SEQ ID NO 1
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 10
<223> OTHER INFORMATION: Xaa is citrulline
```

```
<400> SEQUENCE: 1

Arg Leu Arg Ser Ser Val Pro Gly Val Xaa
1               5                   10

<210> SEQ ID NO 2
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 3,10
<223> OTHER INFORMATION: Xaa is citrulline

<400> SEQUENCE: 2

Arg Leu Xaa Ser Ser Val Pro Gly Val Xaa
1               5                   10

<210> SEQ ID NO 3
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 1,3,10
<223> OTHER INFORMATION: Xaa is citrulline

<400> SEQUENCE: 3

Xaa Leu Xaa Ser Ser Val Pro Gly Val Xaa
1               5                   10

<210> SEQ ID NO 4
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 10
<223> OTHER INFORMATION: Xaa is citrulline

<400> SEQUENCE: 4

Arg Thr Tyr Ser Leu Gly Ser Ala Leu Xaa
1               5                   10

<210> SEQ ID NO 5
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 5,10
<223> OTHER INFORMATION: Xaa is citrulline

<400> SEQUENCE: 5

Gly Ser Ala Leu Xaa Pro Ser Thr Ser Xaa
1               5                   10
```

```
<210> SEQ ID NO 6
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Suppressor of cytokine signalling
      peptide
<220> FEATURE:
<221> NAME/KEY: MOD_RES
<222> LOCATION: 10
<223> OTHER INFORMATION: Xaa is citrulline

<400> SEQUENCE: 6

Pro Ser Gly Asn Gly Gly Glu Gly Thr Xaa
1               5                   10

<210> SEQ ID NO 7
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Alpha 1 Anti trypsin peptide
<220> FEATURE:
<221> NAME/KEY: MOD_RES
<222> LOCATION: 10
<223> OTHER INFORMATION: Xaa is citrulline

<400> SEQUENCE: 7

Leu Ala Glu Phe Ala Phe Ser Leu Tyr Xaa
1               5                   10

<210> SEQ ID NO 8
<211> LENGTH: 9
<212> TYPE: PRT
<213> ORGANISM: Homo sapiens
<220> FEATURE:
<221> NAME/KEY: PEPTIDE
<223> OTHER INFORMATION: citrullinated Versican peptide
<220> FEATURE:
<221> NAME/KEY: MOD_RES
<222> LOCATION: 9
<223> OTHER INFORMATION: Xaa is citrulline

<400> SEQUENCE: 8

Cys Gly Gly Gly Leu Leu Gly Val Xaa
1               5

<210> SEQ ID NO 9
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 9
<223> OTHER INFORMATION: XAA is citrulline

<400> SEQUENCE: 9

Thr Tyr Ser Leu Gly Ser Ala Leu Xaa Pro
1               5                   10

<210> SEQ ID NO 10
<211> LENGTH: 10
<212> TYPE: PRT
<213> ORGANISM: Homo sapiens
<220> FEATURE:
<221> NAME/KEY: PEPTIDE
```

```
<223> OTHER INFORMATION: citrullinated Alpha 1 Anti trypsin peptide
<220> FEATURE:
<221> NAME/KEY: MOD_RES
<222> LOCATION: 8
<223> OTHER INFORMATION: Xaa is citrulline

<400> SEQUENCE: 10

Asp Leu Val Lys Glu Leu Asp Xaa Asp Thr
1               5                   10

<210> SEQ ID NO 11
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated BIGLYCAN peptide
<220> FEATURE:
<221> NAME/KEY: MOD_RES
<222> LOCATION: 10
<223> OTHER INFORMATION: Xaa is citrulline

<400> SEQUENCE: 11

Ile His Glu Lys Ala Phe Ser Pro Leu Xaa
1               5                   10

<210> SEQ ID NO 12
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated BIGLYCAN peptide
<220> FEATURE:
<221> NAME/KEY: MOD_RES
<222> LOCATION: 10
<223> OTHER INFORMATION: Xaa is citrulline

<400> SEQUENCE: 12

Val Pro Lys Gly Val Phe Ser Gly Leu Xaa
1               5                   10

<210> SEQ ID NO 13
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Laminin peptide
<220> FEATURE:
<221> NAME/KEY: MOD_RES
<222> LOCATION: 10
<223> OTHER INFORMATION: Xaa is citrulline

<400> SEQUENCE: 13

Asn Glu Arg Ala Leu Gly Ala Ile Gln Xaa
1               5                   10

<210> SEQ ID NO 14
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated BIGLYCAN peptide
<220> FEATURE:
<221> NAME/KEY: MOD_RES
<222> LOCATION: 10
<223> OTHER INFORMATION: Xaa is citrulline

<400> SEQUENCE: 14
```

Leu Gln Asn Asn Asp Ile Ser Glu Leu Xaa
1               5                   10

<210> SEQ ID NO 15
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated BIGLYCAN peptide
<220> FEATURE:
<221> NAME/KEY: MOD_RES
<222> LOCATION: 10
<223> OTHER INFORMATION: Xaa is citrulline

<400> SEQUENCE: 15

Gln Ala Ile Glu Leu Glu Asp Leu Leu Xaa
1               5                   10

<210> SEQ ID NO 16
<211> LENGTH: 11
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 11
<223> OTHER INFORMATION: Xaa is citrulline

<400> SEQUENCE: 16

Phe Ala Asp Leu Ser Glu Ala Ala Asn Arg Xaa
1               5                   10

<210> SEQ ID NO 17
<211> LENGTH: 10
<212> TYPE: PRT
<213> ORGANISM: Homo sapiens
<220> FEATURE:
<221> NAME/KEY: PEPTIDE
<223> OTHER INFORMATION: citrullinated Vimentin peptide
<220> FEATURE:
<221> NAME/KEY: MOD_RES
<222> LOCATION: 10
<223> OTHER INFORMATION: Xaa is citrulline

<400> SEQUENCE: 17

Leu Gly Asp Leu Tyr Glu Glu Glu Met Xaa
1               5                   10

<210> SEQ ID NO 18
<211> LENGTH: 6
<212> TYPE: PRT
<213> ORGANISM: Homo sapiens
<220> FEATURE:
<221> NAME/KEY: PEPTIDE
<223> OTHER INFORMATION: citrullinated Elastin peptide
<220> FEATURE:
<221> NAME/KEY: MOD_RES
<222> LOCATION: 6
<223> OTHER INFORMATION: Xaa is citrulline

<400> SEQUENCE: 18

Val Leu Pro Gly Ala Xaa
1               5

<210> SEQ ID NO 19
<211> LENGTH: 6

```
<212> TYPE: PRT
<213> ORGANISM: Homo sapiens
<220> FEATURE:
<221> NAME/KEY: PEPTIDE
<223> OTHER INFORMATION: citrullinated Elastin peptide
<220> FEATURE:
<221> NAME/KEY: MOD_RES
<222> LOCATION: 6
<223> OTHER INFORMATION: Xaa is citrulline

<400> SEQUENCE: 19

Gly Gly Val Ala Ala Xaa
1               5

<210> SEQ ID NO 20
<211> LENGTH: 5
<212> TYPE: PRT
<213> ORGANISM: Homo sapiens
<220> FEATURE:
<221> NAME/KEY: PEPTIDE
<223> OTHER INFORMATION: citrullinated CO4a1 peptide
<220> FEATURE:
<221> NAME/KEY: MOD_RES
<222> LOCATION: 5
<223> OTHER INFORMATION: Xaa is citrulline

<400> SEQUENCE: 20

Ile Asp Gly Tyr Xaa
1               5

<210> SEQ ID NO 21
<211> LENGTH: 7
<212> TYPE: PRT
<213> ORGANISM: Homo sapiens
<220> FEATURE:
<221> NAME/KEY: PEPTIDE
<223> OTHER INFORMATION: citrullinated CO5a1 peptide
<220> FEATURE:
<221> NAME/KEY: MOD_RES
<222> LOCATION: 1
<223> OTHER INFORMATION: Xaa is citrulline

<400> SEQUENCE: 21

Xaa Arg Asn Ile Asp Ala Ser
1               5

<210> SEQ ID NO 22
<211> LENGTH: 8
<212> TYPE: PRT
<213> ORGANISM: Homo sapiens
<220> FEATURE:
<221> NAME/KEY: PEPTIDE
<223> OTHER INFORMATION: citrullinated CO5a2 peptide
<220> FEATURE:
<221> NAME/KEY: MOD_RES
<222> LOCATION: 2
<223> OTHER INFORMATION: Xaa is citrulline

<400> SEQUENCE: 22

Gln Xaa Gly Ala His Gly Met Pro
1               5

<210> SEQ ID NO 23
<211> LENGTH: 7
<212> TYPE: PRT
<213> ORGANISM: Homo sapiens
<220> FEATURE:
<221> NAME/KEY: PEPTIDE
<223> OTHER INFORMATION: citrullinated CO5a3 peptide
<220> FEATURE:
<221> NAME/KEY: MOD_RES
```

```
<222> LOCATION: 1
<223> OTHER INFORMATION: Xaa is citrulline

<400> SEQUENCE: 23

Xaa Val Gly Lys Met Gly Arg
1               5

<210> SEQ ID NO 24
<211> LENGTH: 8
<212> TYPE: PRT
<213> ORGANISM: Homo sapiens
<220> FEATURE:
<221> NAME/KEY: PEPTIDE
<223> OTHER INFORMATION: citrullinated CO6a1 peptide
<220> FEATURE:
<221> NAME/KEY: MOD_RES
<222> LOCATION: 2
<223> OTHER INFORMATION: Xaa is citrulline

<400> SEQUENCE: 24

Tyr Xaa Gly Pro Glu Gly Pro Gln
1               5

<210> SEQ ID NO 25
<211> LENGTH: 16
<212> TYPE: PRT
<213> ORGANISM: Artificial sequence
<220> FEATURE:
<223> OTHER INFORMATION: citrullinated immunogenic peptide against SEQ
      ID NO: 1
<220> FEATURE:
<221> NAME/KEY: MOD_RES
<222> LOCATION: 16
<223> OTHER INFORMATION: Xaa is citrulline

<400> SEQUENCE: 25

Lys Leu His Cys Gly Gly Arg Leu Arg Ser Ser Val Pro Gly Val Xaa
1               5                   10                  15

<210> SEQ ID NO 26
<211> LENGTH: 10
<212> TYPE: PRT
<213> ORGANISM: Artificial sequence
<220> FEATURE:
<223> OTHER INFORMATION: random citrullinated control peptide
<220> FEATURE:
<221> NAME/KEY: MOD_RES
<222> LOCATION: 10
<223> OTHER INFORMATION: Xaa is citrulline

<400> SEQUENCE: 26

Asp Gly Val Pro Gly Lys Asp Gly Pro Xaa
1               5                   10

<210> SEQ ID NO 27
<211> LENGTH: 9
<212> TYPE: PRT
<213> ORGANISM: Artificial sequence
<220> FEATURE:
<223> OTHER INFORMATION: non-citrullinated control peptide

<400> SEQUENCE: 27

Arg Leu Arg Ser Ser Val Pro Gly Val
1               5

<210> SEQ ID NO 28
<211> LENGTH: 11
<212> TYPE: PRT
<213> ORGANISM: Artificial sequence
```

```
<220> FEATURE:
<223> OTHER INFORMATION: elongated citrullinated Vimentin peptide of SEQ
      ID NO: 1
<220> FEATURE:
<221> NAME/KEY: MOD_RES
<222> LOCATION: 10
<223> OTHER INFORMATION: Xaa is citrulline

<400> SEQUENCE: 28

Arg Leu Arg Ser Ser Val Pro Gly Val Xaa Leu
1               5                   10

<210> SEQ ID NO 29
<211> LENGTH: 4
<212> TYPE: PRT
<213> ORGANISM: Artificial sequence
<220> FEATURE:
<223> OTHER INFORMATION: citrullinated control peptide
<220> FEATURE:
<221> NAME/KEY: MOD_RES
<222> LOCATION: 4
<223> OTHER INFORMATION: Xaa is citrulline

<400> SEQUENCE: 29

Cys Gly Gly Xaa
1

<210> SEQ ID NO 30
<211> LENGTH: 11
<212> TYPE: PRT
<213> ORGANISM: Artificial sequence
<220> FEATURE:
<223> OTHER INFORMATION: citrullinated synthetic R16Cit peptide
<220> FEATURE:
<221> NAME/KEY: MOD_RES
<222> LOCATION: 6
<223> OTHER INFORMATION: Xaa is citrulline

<400> SEQUENCE: 30

Glu Gly Gly Gly Val Xaa Gly Pro Arg Val Val
1               5                   10

<210> SEQ ID NO 31
<211> LENGTH: 11
<212> TYPE: PRT
<213> ORGANISM: Artificial sequence
<220> FEATURE:
<223> OTHER INFORMATION: citrullinated synthetic R252Cit peptide
<220> FEATURE:
<221> NAME/KEY: MOD_RES
<222> LOCATION: 6
<223> OTHER INFORMATION: Xaa is citrulline

<400> SEQUENCE: 31

Gly Asn Glu Ile Thr Xaa Gly Gly Ser Thr Ser
1               5                   10
```

DETECTION OF DIAGNOSTIC PEPTIDES

The present invention relates to assays for citrullinated peptides in circulation and has relevance to the generation of information of diagnostic significance in relation to a plurality of physiological conditions and diseases.

The modification of the amino acid arginine into citrulline is a posttranslational modification which is facilitated by the presence of PAD enzymes (Peptidyl arginine deiiminase). The presence of citrulline and the modification from arginine is of particular importance in RA patients as a number of autoantibodies have been found to be citrulline specific. These autoantibodies possess an increased specificity and sensitivity compared with conventional markers of RA such as the Rheumatoid Factor.

Even though there is not enough evidence, it is suggested that autoimmunity against collagens and other proteins may be related with pathogenesis in the case of RA and therefore following the path of autoimmunity (autoantigens) could lead to discovery of more evidence of the pathogenesis of the disease.

Citrullination may act as a marker for degradation as it is commonly found in apoptotic bodies.

Whereas the detection of human antibodies to citrullinated peptides, in particular cyclic citrullinated peptides (anti-CCP antibodies) are standard in the laboratory diagnosis and monitoring of rheumatoid arthritis, relatively few studies have addressed the clinical utility of quantitating citrullinated proteins in human serum or plasma.

Takizawa and coworkers (Takizawa et al., 2006), investigated the presence of citrullinated autoantigens in human body fluids. Two monoclonal antibodies, i.e. cF16.1 and cF252.1 raised to synthetic peptides R16Cit (EGGGVR*GPRVV; SEQ ID NO: 30) and R252Cit (GNEITR*GGSTS; SEQ ID NO: 31), respectively, both originating from fibrinogen, were used as coating antibodies in ELISA for detection of citrullinated fibrinogen (R* denotes citrulline substituted from arginine). The exact epitope-specificity of the two monoclonal antibodies was not reported. Positive signals were detected in ELISAs for synovial fluid originating from patients with rheumatoid arthritis, however, all RA (and control) plasma samples remained negative, and Takizawa concluded that fibrinogen is not citrullinated in blood.

The lack of citrullinated fibrinogen in circulation was later confirmed in another study of RA patients (Van Steendam et al., 2010) reporting circulating immune complexes containing fibrinogen-β and fibronectin, but only in non-citrullinated form. In contrast, citrullinated vimentin and minor amounts of fibrinogen-β were detected in immune complexes from synovial fluid of patients with RA.

Chang and coworkers (Chang et al., 2005) reported presence of citrullinated fibronectin in plasma of RA patients. Although the levels were not quantitated they were reported to be higher in RA plasma compared to healthy controls and patients with systemic lupus erythematosus (SLE). They used a sandwich ELISA employing a monoclonal antibody binding to human fibronectin (Abcam) as coater and for detector an anti-citrulline rabbit antibody (Biogenesis) was used. Characterization of the fibronectin molecules detected by the sandwich assay was not provided. However, the antibodies incorporated into the assay would not serve to quantitate specific proteolytic, citrullinated fibronectin neoepitopes, as these could neither be distinguished from intact citrullinated fibronectin nor from citrullinated fibronectin fragments sharing the epitope in the heparin-binding domain recognized by the coating antibody.

Also, Zhao and coworkers (Zhao et al., 2008) reported presence of citrullinated fibrinogen in high molecular weight immune complexes originating from RA plasma. Briefly, following fractionation of immune complexes obtained from RA plasma samples, presence of citrullinated fibrinogen was determined using an anti-citrulline detection kit on immunoblots (Upstate, Chicago, Ill., USA). Such bands were absent in corresponding immunoblots from healthy control plasma.

Tilleman et al. (2008) reported the presence of fragments of citrullinated vimentin in synovial cytosolic protein extracts obtained from patients with inflammatory arthritis, mainly rheumatoid arthritis. By mass spectrometry, citrullinated fibrinogen, citrullinated fibronectin and citrullinated vimentin were detected in synovial fluid of patients with RA (Tabushi et al., 2008).

The majority of autoantibodies in RA are also found in patients with other diseases, and therefore have a limited diagnostic utility. However, some (relatively) specific autoantigens have been described, in particular those carrying citrullinated residues, and these includes; citrullinated filaggrin, citrullinated vimentin and cyclic citrullinated peptides (van Galen et al., 2005; Schellekenes at al., 1998)

Lundgren et al. (2005) suggest citrullinated type II collagen may carry significant arthritogenic potential. A subsequent report confirmed the presence of a citrullinated triple helical type II collagen epitope in synovial fluid of RA patients (Uysal et al., 2009), and autoimmunity to type II collagen (both native and citrullinated) was proposed to be an important factor in RA pathogenicity. Detection of the citrullinated type II collagen in synovial fluid was accomplished using monoclonal antibodies to native type II collagen as capture and monoclonal ACC2 binding to citrullinated type II collagen as detector antibody. The latter antibody was cross-reactive with citrullinated fibrinogen (Uysal et al., 2009).

Quantification of the citrulline level in circulation, following deproteinisation and quantification by high-performance liquid chromatography (HPLC), was reported to be a physiological marker of small bowel epithelial radiation damage (Lutgens et al., 2003).

We have now established that citrullinated peptides can be detected in blood or fluid components thereof such as plasma using antibodies that have specificity for an epitope that combines the presence of citrulline with a terminal amino acid sequence of the peptide. We hypothesise that protein fragments preferentially survive in the circulation when citrulline is present at or close to an end of the fragment. Use of an antibody having specificity for citrulline in the context of a specific amino acid sequence allows detection of peptides originating as fragments of a specific protein from which the amino acid sequence derives. This may be due to the citrullination conferring altered resistance to degradation by various proteinases. Quantitation of such peptides allows diagnostic information to be obtained relating to various disease states in which production and/or degradation of the relevant protein is altered.

Accordingly, the present invention now provides a method of assay for citrullinated fragments of a protein in a sample comprising blood or a fluid component thereof, comprising contacting a said sample with an antibody or a fragment thereof having specific binding affinity for citrullinated fragments of said protein having a terminal antibody binding site comprising citrulline, such that binding of the antibody of antibody fragment requires the presence in said binding site of both a specific terminal amino acid sequence and said citrulline, and detecting binding of said antibody to said protein fragments. The citrulline may be in a fully terminal position in said sequence and this may be required for antibody binding. The location of the epitope may be N-terminal or C-terminal. Preferably, the amino acid sequence required by the antibody is specific to the protein.

Preferably, said antibody or a fragment thereof has specific binding affinity for citrullinated fragments of vimentin having a terminal antibody binding site comprising citrulline, such that binding of the antibody of antibody fragment requires the presence a terminal vimentin amino acid sequence containing citrulline, and detecting binding of said antibody to said vimentin fragments.

Preferably, said antibody or a fragment thereof has specific binding affinity for citrullinated fragments of SOCS-2, Alpha 1 anti tyrpsin, versican, biglycan, or laminin, having a terminal antibody binding site comprising citrulline, such that binding of the antibody of antibody fragment requires the presence a terminal amino acid sequence specific for said protein containing citrulline, and detecting binding of said antibody to said fragments.

Alternatively, said antibody or a fragment thereof has specific binding affinity for citrullinated fragments of elastin or collagen types V and VI having a terminal antibody binding site comprising citrulline, such that binding of the antibody of antibody fragment requires the presence a terminal amino acid sequence specific for said protein containing citrulline, and detecting binding of said antibody to said fragments.

Said detection of binding is preferably quantative. Typically, the amount of binding is compared to control values established for populations of healthy individuals and of individuals characterised by a fibrotic disease or by rheumatoid arthritis.

The method may be conducted as a competition assay such that peptides in said sample compete for binding to the antibody or antibody fragment with a known concentration of a binding agent which binds said antibody or antibody fragment.

Diseases in which altered levels of citrullinated peptides may be detected in blood or its components will include rheumatoid arthritis and various diseases involving fibrosis, such as Liver fibrosis, Skin fibrosis and Lung Fibrosis. Proteins of relevance, disease states and proteinases involved in the generation of particular exemplary peptide terminal sequences are listed in the following table:

TABLE 1

| Protein | Protease | Disease | Sequence | SEQ ID NO: |
|---|---|---|---|---|
| Vimentin | MMP2, 8 | RA, Fibrosis | 69'RLRSSVPGVCit↓ | 1 |
| | | | 69'RLCitSSVPGVCit↓ | 2 |
| | | | 69'CitLCitSSVPGVCit↓ | 3 |
| Vimentin | MMP; not specified | Fibrosis, RA | 36'RTYSLGSALCit↓ | 4 |
| Vimentin | MMP; not specified | Fibrosis, RA | 41'GSALCitPSTSCit↓ | 5 |
| Suppressor of cytokine signalling 2 (SOCS-2) | MMP (type not specified) | Fibrosis, RA | 8'PSGNGGEGTCit↓ | 6 |
| Alpha 1 Anti trypsin (A1AT) | MMP; not specified | Fibrosis, RA | 54'LAEFAFSLYCit↓ | 7 |
| Versican | MMP; not specified | Fibrosis, RA | 315'CGGGLLGVCit↓ | 8 |

Other citrullinated peptides that may be detected according to the present invention include those containing the following terminal sequences:

| | | SEQ ID NO: |
|---|---|---|
| Vimentin | 37'TYSLGSAL-CIT-P↓ | 9 |
| A1AT | 195'DLVKELD-CIT-DT↓ | 10 |
| BIGLYCAN | 129'IHEKAFSPL-CIT↓ | 11 |
| BIGLYCAN | 174'VPKGVFSGL-CIT↓ | 12 |

Other sequences that may be targeted are as set out in the following table:

TABLE 2

| | | | SEQ ID NO: |
|---|---|---|---|
| Laminin 2059' NERALGAIQ-Cit↓ 2068' | | Human | Fibrosis | 13 |
| Biglycan 97' LQNNDISEL-Cit↓ 106' | | Human, Rat, Mouse | Fibrosis | 14 |
| Biglycan 242' QAIELEDLL-Cit↓ 251' | | Human, Mouse | Fibrosis | 15 |
| Vimentin 295' FADLSEAANR-Cit↓ 304' | | Human, Mouse, Rat | Fibrosis, RA, Atherosclerosis, Cancer | 16 |
| Vimentin 146' LGDLYEEEM-Cit↓ 155' | | Human, Mouse, Rat | Fibrosis, RA, Athero clerosis, Cancer | 17 |

Still further sequences the may be targeted are set out in the following table:

TABLE 3

| Protein | Protease | Disease(s) | Sequence | SEQ ID NO: |
|---|---|---|---|---|
| Elastin | MMP9 | CVD, Fibrosis | ... VLPGA-CIT↓ (CIT at position 159) | 18 |
| Elastin | MMP9 | CVD, Fibrosis | ... GGVAA-CIT↓ (CIT at position 762) | 19 |
| CO4a1 | FAP | | ↓IDGY-CIT-GPPGP ... (CIT at position 476) | 20 |
| CO5a1 | MMP2/MMP9 | CVD, Fibrosis | ↓CIT-RNIDAS ... (CIT at position 1584) | 21 |
| CO5a2 | MMP2/MMP9 | CVD, Fibrosis | ↓Q-CIT-GAHGMP ... (CIT at position 356) | 22 |
| CO5a3 | MMP9 | CVD, Fibrosis | ↓CIT-VGKMGR ... (CIT at position 525) | 23 |
| CO6a1 | MMP2 | CVD, Fibrosis | ↓Y-CIT-GPEGPQ ... (CIT at position 573) | 24 |

The assay may be conducted using a competition assay format of any known type, including an ELISA format or RIA format.

Antibodies and antibody fragments that may be employed in place of whole antibodies include a monoclonal or polyclonal antibody or immunoreactive fragment thereof (i.e. capable of binding the same antigenic determinant), including—but not limited to—Fab, Fab', and F(ab')2 fragments.

The invention further provides an antibody or antibody fragment specifically binding peptide fragments of a protein such that for specific binding said fragments are required to have an antibody specific N-terminal or C-terminal amino acid sequence which comprises at least one citrulline. Such an antibody or antibody fragment may be specific for any one of the terminal amino acid sequences shown above.

The invention will be further illustrated and explained by the following Examples.

EXAMPLE 1

In order to examine the presence of citrullinated proteins in fibrotic tissue, a number of western blot experiments were carried out using the Citrulline Detection kit from Upstate which utilizes an anti-modified citrulline antibody. This antibody will react with a peptide including citrulline without regard for the amino acid sequence in which the citrulline occurs.

Three different categories of fibrotic samples were analysed. Liver tissue from $CCl_4$ treated rats, Skin from Bleomycin treated mice and fibrotic lung tissue were each extracted using the following protocol. Tissue was deep frozen with liquid nitrogen and pulverised in a steel mortar. It was then diluted in 0.5M acetic acid solution in which protease inhibitors from ROCHE and was left overnight at 4° C. under gentle shaking. Solution was then sonicated at 60% amplitude with 5 pulses of 3 seconds each. Concentration was calculated and solution was stored at −80 degrees. Reactive bands represent citrulline specific reactivity in a variety of different molecular weights. A number of the reacting bands are common among different tissue, whereas other bands are unique to diseased tissue. 15 diseased and 5 control samples of each tissue were used. Representative results are seen in FIG. 1.

Figure 1:
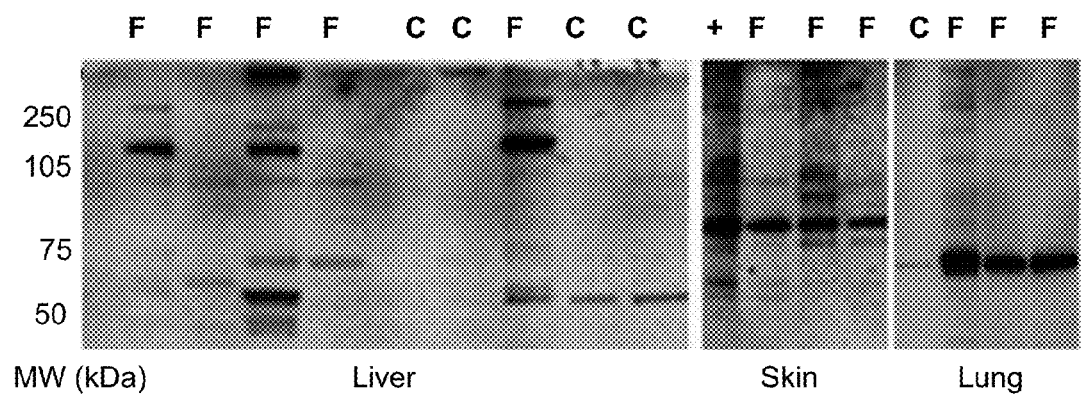
FIG. 1 shows citrullinated proteins detected by antibodies in the Millipore anti-citrulline kit in Western Blots of extracts of fibrotic liver, skin and lung.
Figure 2:
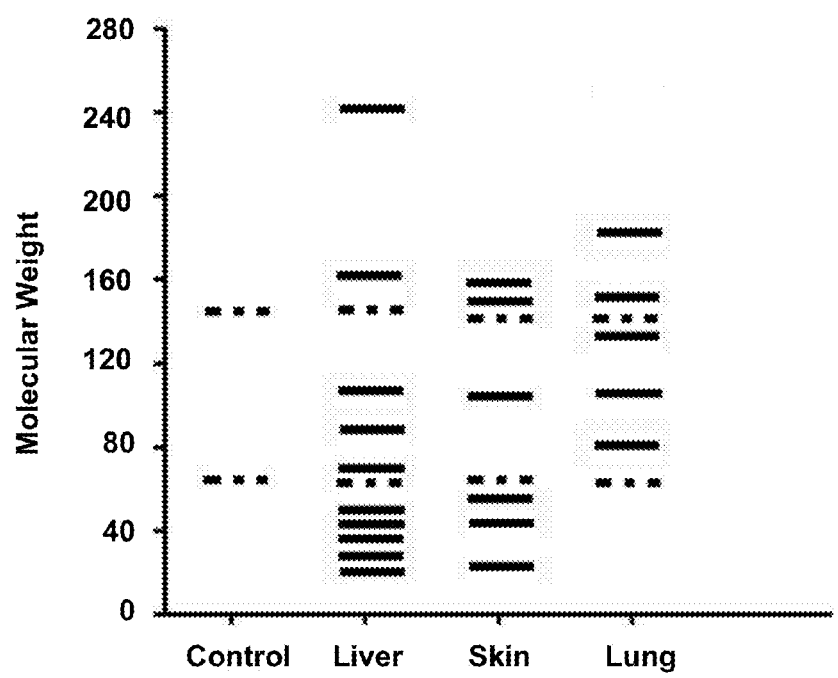
FIG. 2 shows a schematic and simplified summary of the data from FIG. 1 of citrulline specific reactivity in 3 different fibrotic tissues. While dotted bands indicate presence of molecules detected in both healthy and diseased tissue, the solid bands indicate disease-specific (fibrotic) fragments carrying citrulline residues.

A schematic and simplified representation of the data in FIG. 1 is displayed in FIG. 2 indicating all disease specific citrullinated proteins (solid) and the ones also found in controls (dotted) was devised in order to analyse the collective results of FIG. 1.

The collective preliminary results indicate a strong presence of citrullinated proteins in diseased tissue which are not present in healthy tissue. Such citrullinated proteins/fragments could potentially serve as biomarkers for selected diseases.

EXAMPLE 2

Monoclonal antibodies were raised using conventional techniques against the citrullinated vimentin sequence RLRSSVPGV-Cit by immunisation with KLH-CGG-RLRSSVPGV-Cit (SEQ ID NO: 25) and screening for reactivity with Biotin-RLRSSVPGV-Cit. The specificity of the antibodies was subsequently assessed in a competition ELISA as described below.

A streptavidin-coated microtitre plate (Roche) was incubated with 100 µL/well of a buffer 25 mM Tris-BTB (BSA, Tween 20, and Bronidox) coating buffer containing 5 ng/ml of Bio-RLRSSVPGV-Cit. After incubation for 30 minutes at 20° C. with shaking, it was then washed 5 times and 20 µL/well of the standard (synthetic peptide RLRSSVPGV-Cit), QC samples and diluted unknown samples were added. Subsequently, to each well 100 µL of monoclonal antibody diluted to 120 ng/ml in incubation buffer was added and the plate was incubated for 1 h at 20 C with shaking. After washing, 100 µL of HRP-labelled goat anti-mouse immunoglobulin was added to each well and the plate was incubated for 1 hour at 20 C with shaking. This was followed by 5 times washing step after which 100 µL/well TMB (TMB: Kem-En-Tec cat. 4380-100-125) was added and incubated for 15 min at 20° C. in darkness with shaking. Finally, 100 µL/well of stopping solution was added to each well and the samples were read at 450 nm ELISA reader with 650 nm as reference.

Figure 3A:
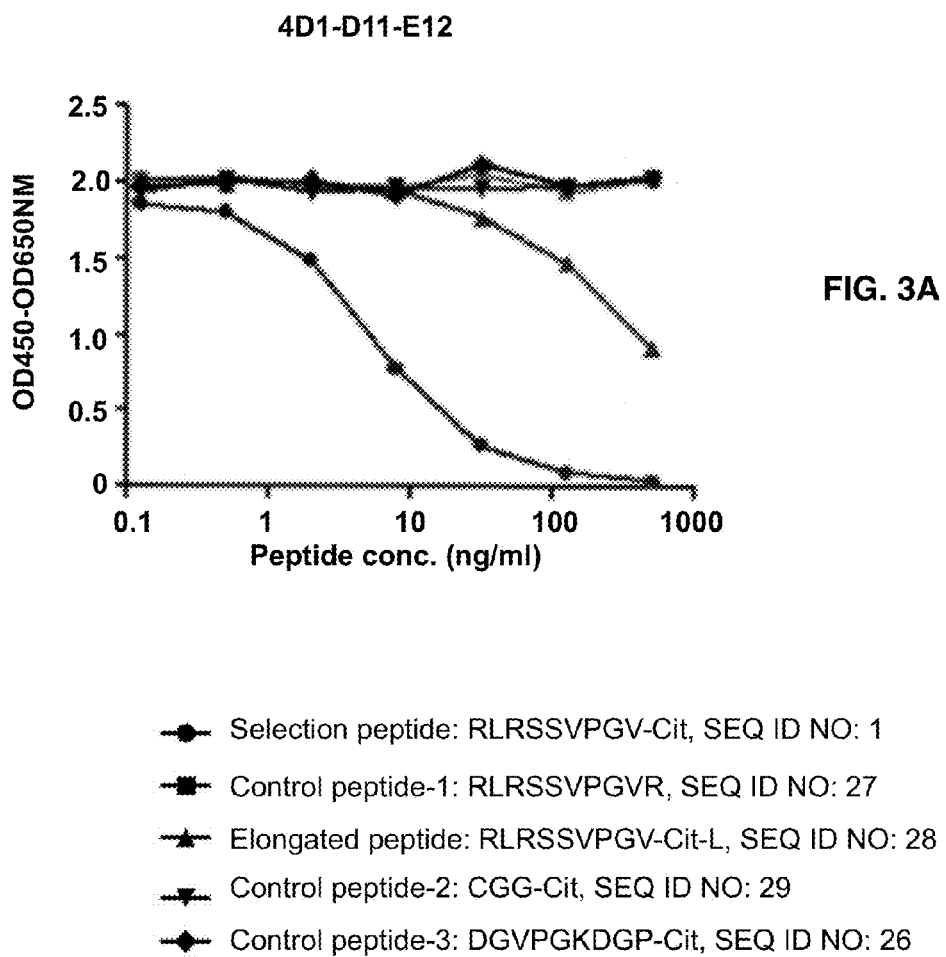
FIGS. 3A-3B show results obtained in Example 2 showing the specific reactivity of two monoclonal antibodies raised against the citrullinated vimentin peptide sequence RLRSSVPGV-Cit to the selection peptide and some cross-reactivity to the elongated peptide. Binding to the non-citrullinated peptide RLRSSVPGV could not be detected.
Figure 3B:
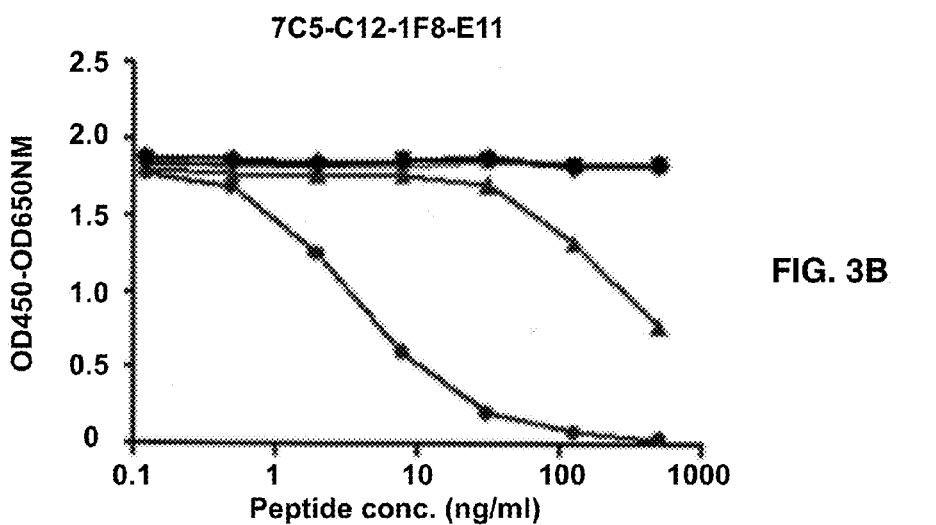

The reactivity of a selected monoclonal antibody NB212 against chosen peptides was evaluated in a competition assay employing a peptide of the sequence RLRSSVPGV-Cit bound to a microtiter plate and the chosen peptide in solution competing for binding to the monoclonal antibody. Results are shown in FIGS. 3A-3B. It can be seen that the antibody does not bind to a peptide of random sequence having a terminal citrulline residue (DGVPGKDGP-Cit; SEQ ID NO: 26), does not bind to the target amino acid sequence RLRSSVPGV (SEQ ID NO: 27)without the terminal citrulline, and binds only weakly to an elongated version of the target peptide RLRSSVPGV-Cit-L (SEQ ID NO: 28). The antibody therefore binds specifically an epitope containing both citrulline (in this case in the terminal position) and the vimentin amino acid sequence.

EXAMPLE 3

An ELISA was performed essentially as described above with reference to FIGS. 3A-3B, however human serum samples were pre-diluted 1:8 in 10 mM PBS-BTB buffer prior to addition to the wells in duplicate.

Figure 4A:
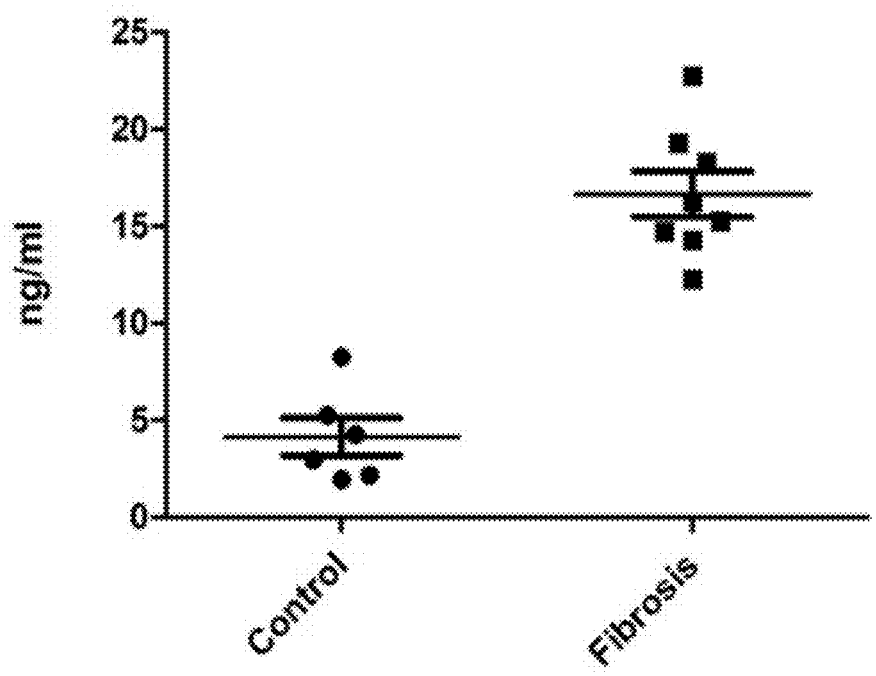
FIGS. 4A-4B shows elevated concentrations of citrullinated peptide fragments originating from vimentin between healthy controls and liver fibrosis diagnosed patients (FIG. 4A) and between healthy controls and rheumatoid arthritis diagnosed patients (FIG. 4B) and detected in the NB212 ELISA.
Figure 4B:
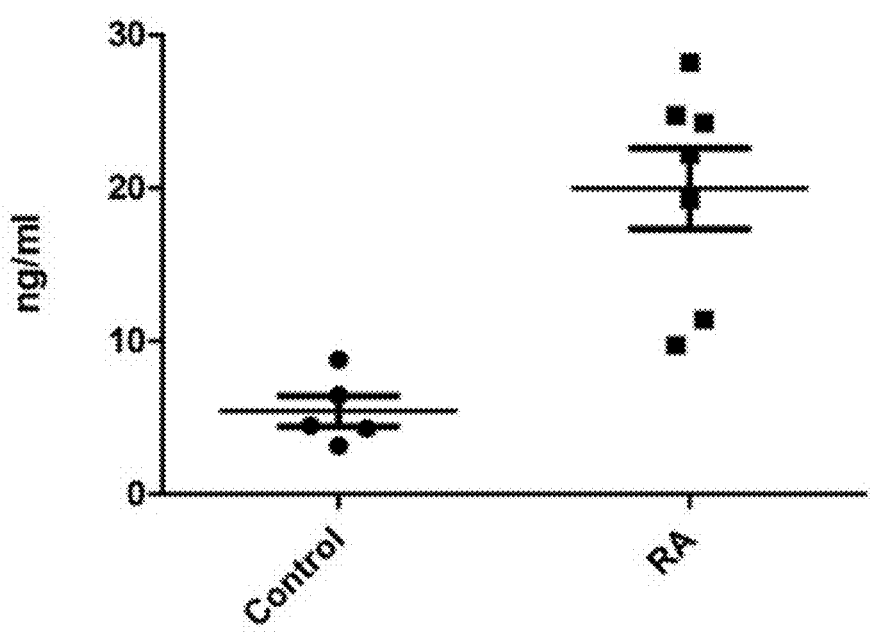

Eight serum samples were obtained from subjects with diagnosed liver fibrosis and these were tested in the ELISA with six samples from healthy volunteers serving as controls. In a second experiment, seven serum samples from patients with rheumatoid arthritis (RA) were compared to five controls. Results are shown in FIGS. 4A-4B.

Dramatic elevation of circulating citrullinated peptide fragments originating from vimentin (as detected by monoclonal antibody NB212) is observed in both subjects with liver fibrosis and patients with rheumatoid arthritis. In contrast, relatively low levels of these citrullinated molecules are found in the blood of healthy control subjects.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

Takizawa Y, Suzuki A, Sawada T, Ohsaka M, Inoue T, Yamada R, Yamamoto K. Citrullinated fibrinogen detected as a soluble citrullinated autoantigen in rheumatoid arthritis synovial fluids. Ann Rheum Dis. 2006 August; 65(8):1013-20. Epub 2006 Jan. 31.

Chang X, Yamada R, Suzuki A, Kochi Y, Sawada T, Yamamoto K Rheumatology (Oxford). 2005 November; 44(11):1374-82. Epub 2005 Aug. 16. Citrullination of fibronectin in rheumatoid arthritis synovial tissue.

Van Steendam K, Tilleman K, De Ceuleneer M, De Keyser F, Elewaut D, Deforce D. Citrullinated vimentin as an important antigen in immune complexes from synovial fluid of rheumatoid arthritis patients with antibodies against citrullinated proteins. Arthritis Res Ther. 2010;12 (4):R132. Epub 2010 Jul. 7.

Tabushi Y, Nakanishi T, Takeuchi T, Nakajima M, Ueda K, Kotani T, Makino S, Shimizu A, Hanafusa T, Takubo T. Detection of citrullinated proteins in synovial fluids derived from patients with rheumatoid arthritis by proteomics-based analysis. Ann Clin Biochem. 2008 July; 45(Pt 4):413-7.

Tilleman K, Van Steendam K, Cantaert T, De Keyser F, Elewaut D, Deforce D. Synovial detection and autoantibody reactivity of processed citrullinated isoforms of vimentin in inflammatory arthritides. Rheumatology (Oxford). 2008 May; 47(5):597-604.

Lundberg K, Nijenhuis S, Vossenaar E R, Palmblad K, van Venrooij W J, Klareskog L, Zendman A J, Harris H E. Citrullinated proteins have increased immunogenicity and arthritogenicity and their presence in arthritic joints correlates with disease severity. Arthritis Res Ther. 2005;7 (3):R458-67. Epub 2005 Feb. 21.

van Gaalen F A, Visser H, Huizinga T W. A comparison of the diagnostic accuracy and prognostic value of the first and second anti-cyclic citrullinated peptides (CCP1 and CCP2) autoantibody tests for rheumatoid arthritis. Ann Rheum Dis. 2005 October; 64(10):1510-2. Epub 2005 Mar. 30.

Lutgens L C, Deutz N E, Gueulette J, Cleutjens J P, Berger M P, Wouters B G, von Meyenfeldt M F, Lambin P. Citrulline: a physiologic marker enabling quantitation and monitoring of epithelial radiation-induced small bowel damage. Int J Radiat Oncol Biol Phys. 2003 Nov. 15; 57(4):1067-74.

Schellekens G A, de Jong B A, van den Hoogen F H, van de Putte L B, van Venrooij W J. Citrulline is an essential constituent of antigenic determinants recognized by rheumatoid arthritis-specific autoantibodies. J Clin Invest. 1998 Jan. 1; 101(1): 273-81.

Uysal H, Bockermann R, Nandakumar K S, Sehnert B, Bajtner E, Engström A, Serre G, Burkhardt H, Thunnissen M M, Holmdahl R. Structure and pathogenicity of antibodies specific for citrullinated collagen type II in experimental arthritis. J Exp Med. 2009 Feb. 16; 206(2):449-62. Epub 2009 Feb. 9.

Zhao X, Okeke N L, Sharpe O, Batliwalla F M, Lee A T, Ho P P, Tomooka B H, Gregersen P K, Robinson W H. Circulating immune complexes contain citrullinated fibrinogen in rheumatoid arthritis. Arthritis Res Ther. 2008; 10(4):R94. Epub 2008 Aug. 18. PubMed PMID: 18710572;

The invention claimed is:

1. A method of diagnosis or of quantitation of rheumatoid arthritis or fibrosis comprising;

obtaining a patient sample comprising blood or a fluid component thereof;

conducting an immunoassay to measure fragments of a protein having an N- or C-terminal neo-epitope formed by cleavage of said protein by a protease, said N- or C-terminal neo-epitope comprising at least one citrulline residue, and said fragments being naturally present in said patient sample, and;

associating an elevation of said measure in said patient above a normal level with the presence or extent of rheumatoid arthritis or fibrosis, wherein said immunoassay is conducted by a method comprising:

contacting the fragments of a protein having an N- or C-terminal neo-epitope comprising at least one citrulline residue that are naturally present in said sample with an isolated antibody or an isolated antibody fragment thereof having specific binding affinity for said fragments of said protein having said N- or C-terminal neo-epitope comprising at least one citrulline residue but not reactive with an intact protein, and measuring the extent of binding of said N- or C-terminal neo-epitope comprising at least one citrulline residue to said antibody or antibody fragment thereof to measure therein fragments having said neo-epitope comprising at least one citrulline residue, wherein said antibody or antibody fragment thereof specifically binds to an N- or C-terminal neo-epitope amino acid sequence formed by cleavage of the intact protein by a protease, said C-terminal neo-epitope amino acid sequence comprising said at least one citrulline residue and having any one of the following sequences:

| Sequence | SEQ ID NO: |
|---|---|
| RLRSSVPGVCit↓ | 1 |
| RLCitSSVPGVCit↓ | 2 |
| CitLCitSS-VPGVCit↓ | 3 |
| PSGNGGEGTCit↓ | 6 |
| RTYSLGSALCit↓ | 4 |
| GSALCitPSTSCit↓ | 5 |
| LAEFAFSLYCit↓ | 7 |
| CGGGLLGVCit↓ | 8 |
| TYSLGSAL-Cit-P↓ | 9 |
| DLVKELD-Cit-DT↓ | 10 |
| IHEKAFSPL-Cit↓ | 11 |
| VPKGVFSGL-Cit↓ | 12 |
| NERALGAIQ-Cit↓ | 13 |
| LQNNDISEL-Cit↓ | 14 |
| QAIELEDLL-Cit↓ | 15 |
| FADLSEAANR-Cit↓ | 16 |
| LGDLYEEEM-Cit↓ | 17 |
| . . . VLPGA-Cit↓ | 18 |
| . . . GGVAA-Cit↓ | 19 | or said N-terminal neo-epitope amino acid sequence comprising said at least one citrulline residue and having any one of the following sequences:

| Sequence | SEQ ID NO: |
|---|---|
| ↓IDGY-Cit-GPPGP . . . | 20 |
| ↓Cit-RNIDAS . . . | 21 |
| ↓Q-Cit-GAHGMP . . . | 22 |
| ↓Cit-VGKMGR . . . | 23 |
| ↓Y-Cit-GPEGPQ . . . | 24. |

2. A method as claimed in claim 1, wherein the protein is vimentin.

3. A method as claimed in claim 1, wherein protein is SOCS-2, Alpha 1 anti tyrpsin, versican, biglycan, or laminin.

4. A method as claimed in claim 1, wherein the protein is elastin, collagen type V or collagen type VI.

5. A method as claimed in claim 1, conducted as a competition assay such that fragments of a protein in said sample compete for binding to the antibody or antibody fragment thereof with a known concentration of a binding agent which binds said antibody or antibody fragment.

6. An isolated antibody or isolated antibody fragment thereof specifically binding fragments of a protein having an N-terminal or C-terminal neo epitope amino acid sequence formed by cleavage of an intact protein by a protease, wherein said isolated antibody or isolated antibody fragment thereof is not reactive with an intact protein, and wherein said isolated antibody or isolated antibody fragment thereof is specific for any one of the following C-terminal amino acid sequences comprising at least one citrulline residue:

| Sequence | SEQ ID NO: |
|---|---|
| RLRSSVPGVCit↓ | 1 |
| RLCitSSVPGVCit↓ | 2 |
| CitLCitSS-VPGVCit↓ | 3 |
| PSGNGGEGTCit↓ | 6 |
| RTYSLGSALCit↓ | 4 |
| GSALCitPSTSCit↓ | 5 |
| LAEFAFSLYCit↓ | 7 |
| CGGGLLGVCit↓ | 8 |
| TYSLGSAL-Cit-P↓ | 9 |
| DLVKELD-Cit-DT↓ | 10 |
| IHEKAFSPL-Cit↓ | 11 |
| VPKGVFSGL-Cit↓ | 12 |
| NERALGAIQ-Cit↓ | 13 |
| LQNNDISEL-Cit↓ | 14 |
| QAIELEDLL-Cit↓ | 15 |
| FADLSEAANR-Cit↓ | 16 |
| LGDLYEEEM-Cit↓ | 17 |
| . . . VLPGA-Cit↓ | 18 |
| . . . GGVAA-Cit↓ | 19 | or any one of the following N-terminal sequences comprising at least one citrulline residue:

| Sequence | SEQ ID NO: |
|---|---|
| ↓IDGY-Cit-GPPGP . . . | 20 |
| ↓Cit-RNIDAS . . . | 21 |
| ↓Q-Cit-GAHGMP . . . | 22 |
| ↓Cit-VGKMGR . . . | 23 |
| ↓Y-Cit-GPEGPQ . . . | 24. |

7. An isolated antibody or isolated antibody fragment thereof as claimed in claim 6, wherein said protein is vimentin.

8. An isolated antibody or isolated antibody fragment thereof as claimed in claim 6, wherein the protein is SOCS-2, Alpha 1 anti tyrpsin, versican, biglycan, or laminin.

9. An isolated antibody or isolated antibody fragment thereof as claimed in claim 6, wherein the protein is elastin, collagen type V or collagen type VI.

* * * * *